(12) United States Patent
Sanford et al.

(10) Patent No.: US 6,632,225 B2
(45) Date of Patent: Oct. 14, 2003

(54) METHOD AND APPARATUS FOR RESECTING A DISTAL FEMUR AND A PROXIMAL TIBIA IN PREPARATION FOR IMPLANTING A PARTIAL KNEE PROSTHESIS

(75) Inventors: Adam H. Sanford, Warsaw, IN (US); Toby N. Farling, Warsaw, IN (US); Robert A. Hodorek, Warsaw, IN (US); Mark A. Price, Warsaw, IN (US); Paul L. Saenger, Asheville, NC (US); Richard V. Williamson, Ana Cortes, WA (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 09/885,864

(22) Filed: Jun. 20, 2001

(65) Prior Publication Data
US 2002/0198530 A1 Dec. 26, 2002

(51) Int. Cl.⁷ .................................................. A61F 5/00
(52) U.S. Cl. ............................................ 606/87; 606/90
(58) Field of Search ............................... 606/87, 62, 90, 606/99, 98, 86, 89, 104, 105; 623/17.11, 17.16, 18.11, 16.11; D24/140, 133, 135

(56) References Cited

U.S. PATENT DOCUMENTS

| | | | | |
|---|---|---|---|---|
| 5,213,112 A | * | 5/1993 | Niwa et al. ................ 600/587 |
| 5,968,050 A | * | 10/1999 | Torrie ........................ 606/87 |
| 6,063,088 A | * | 5/2000 | Winslow ..................... 606/61 |
| 6,086,595 A | * | 7/2000 | Yonemura et al. ........... 606/99 |
| 6,264,657 B1 | * | 7/2001 | Urbahns et al. ............. 606/61 |
| D457,957 S | * | 5/2002 | Sanford et al. ........... D24/140 |

* cited by examiner

Primary Examiner—Pedro Philogene
(74) Attorney, Agent, or Firm—Botkin & Hall, LLP

(57) ABSTRACT

A method of resecting a proximal tibia and distal femur for implanting a partial knee prosthesis uses a resecting kit which includes multiple spacers, each of which has a different spacing dimension. A surgeon selects the appropriate spacer with the amount of correction desired to align the patient's leg and installs the spacer with the spacing dimension between the distal femur and proximal tibia which is to receive the partial knee prosthesis. The spacers have projecting stems, upon which a resector is installed. The resector is then aligned with the axis selected by the surgeon according to known methods, and is pinned to the femur and proximal tibia. A distal femoral cut is then made in the femur after which the resector is removed while leaving at least two of the pins in place, the pins being headless pins. A second resector is then installed on the pins to effect the required cut of the tibia. Additional cuts are made in the femur according to known procedures, and the femoral and tibial prostheses are then installed, according to known procedures.

15 Claims, 9 Drawing Sheets

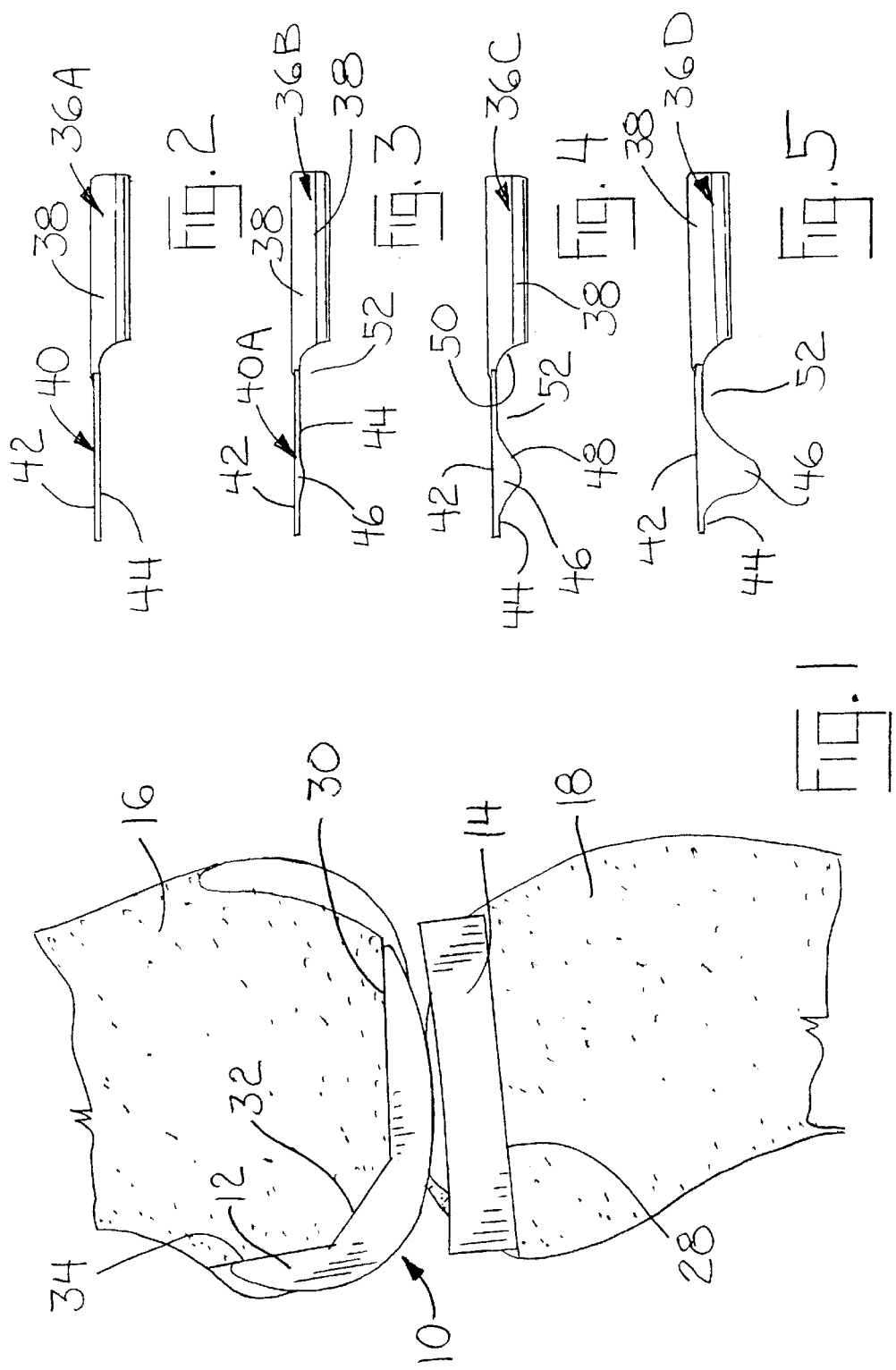

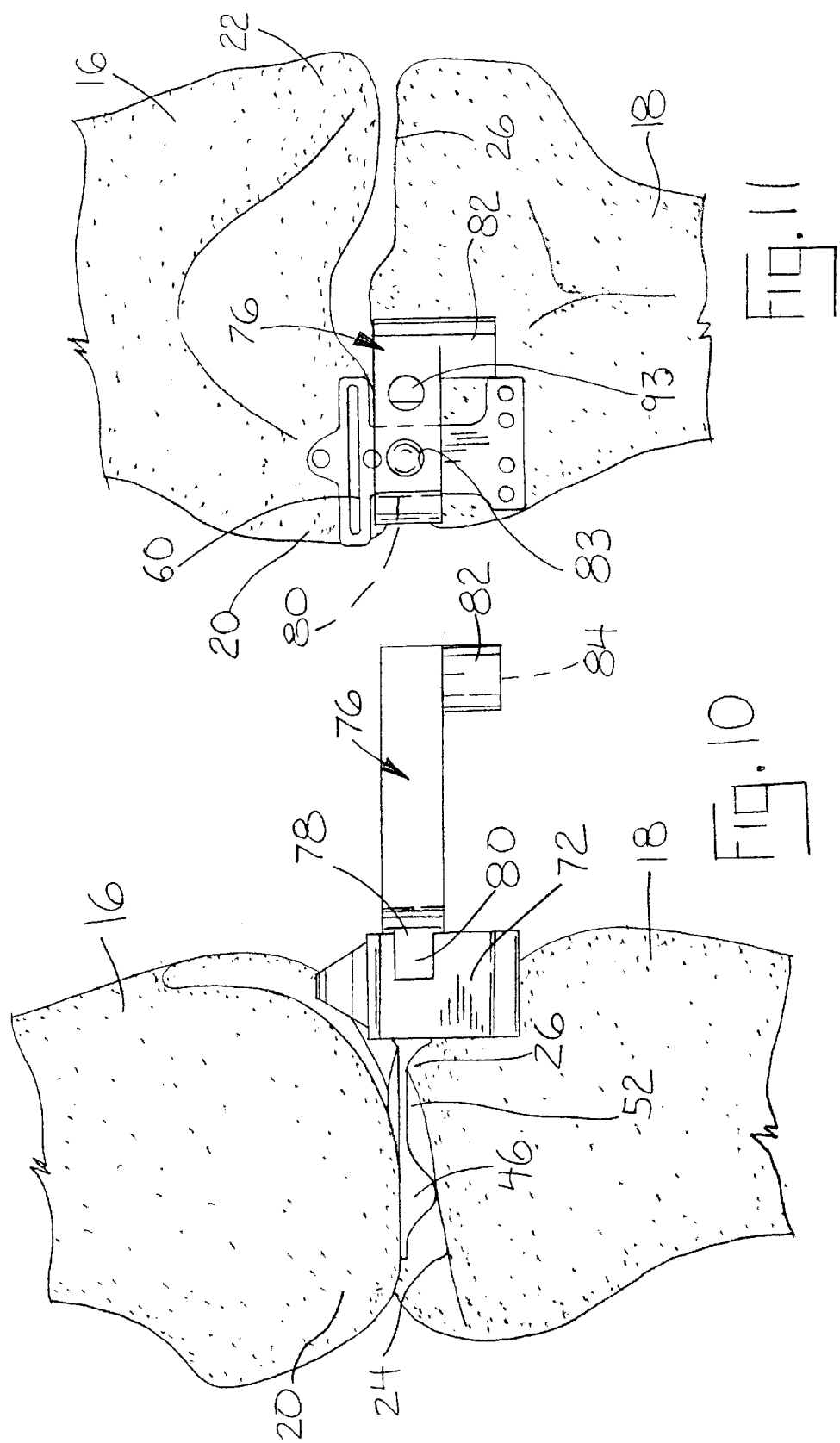

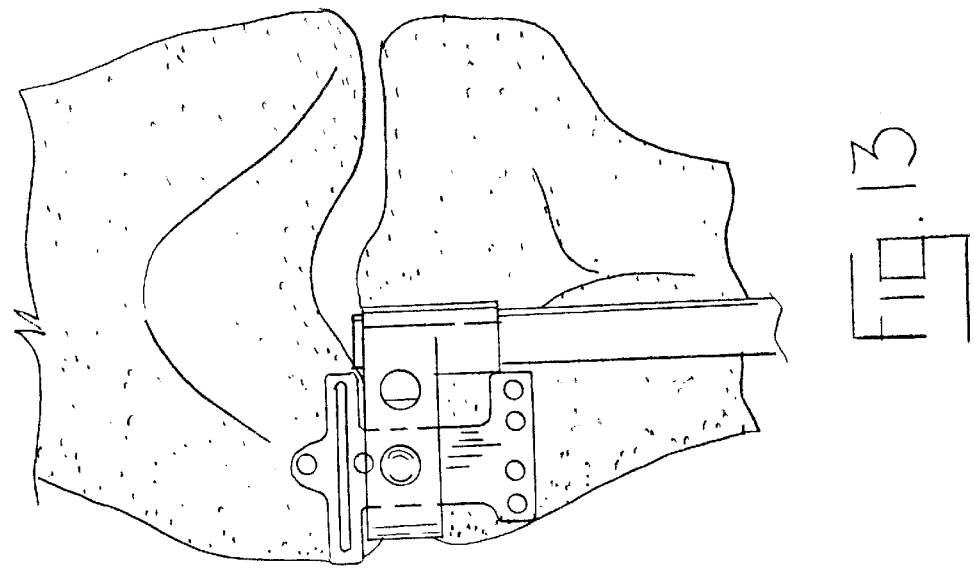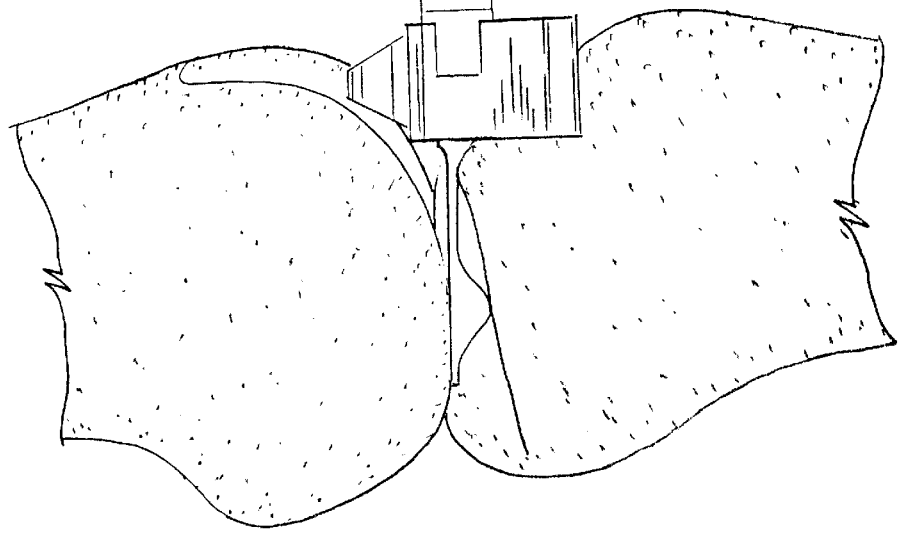

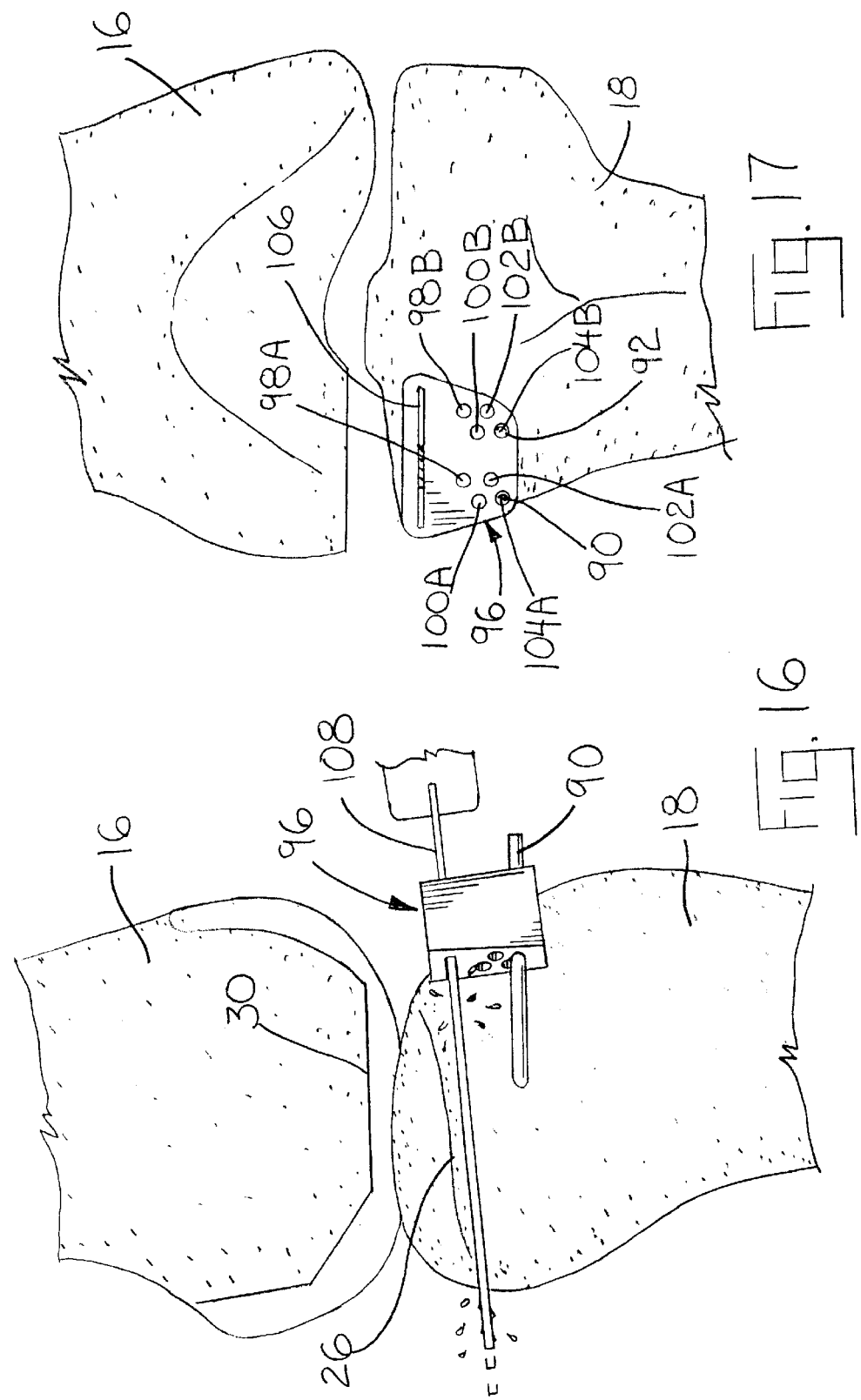

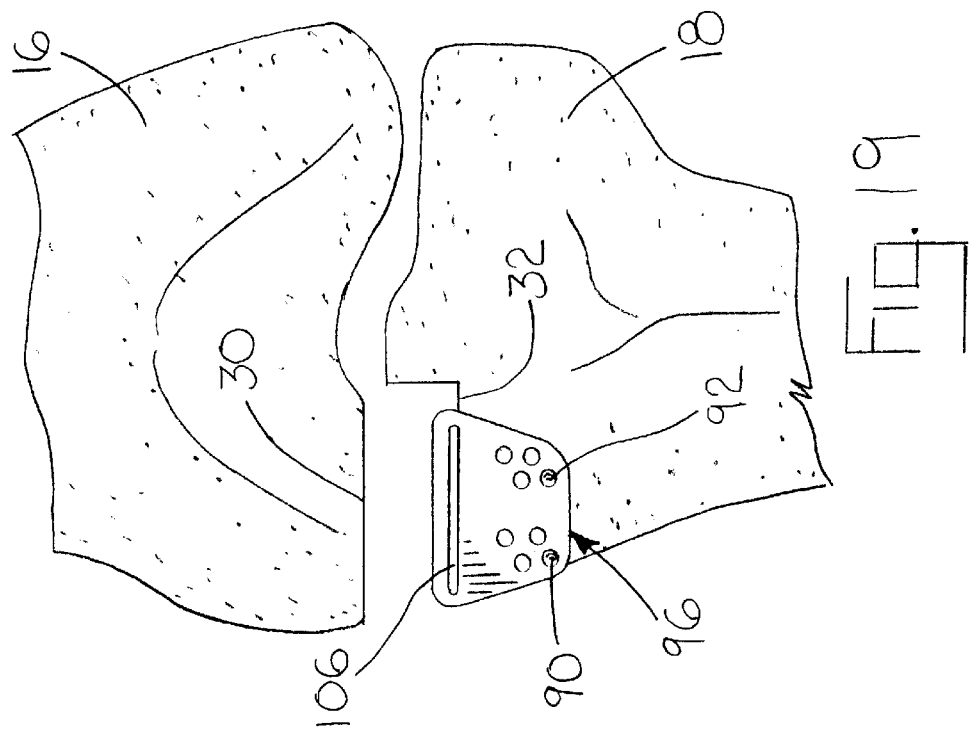
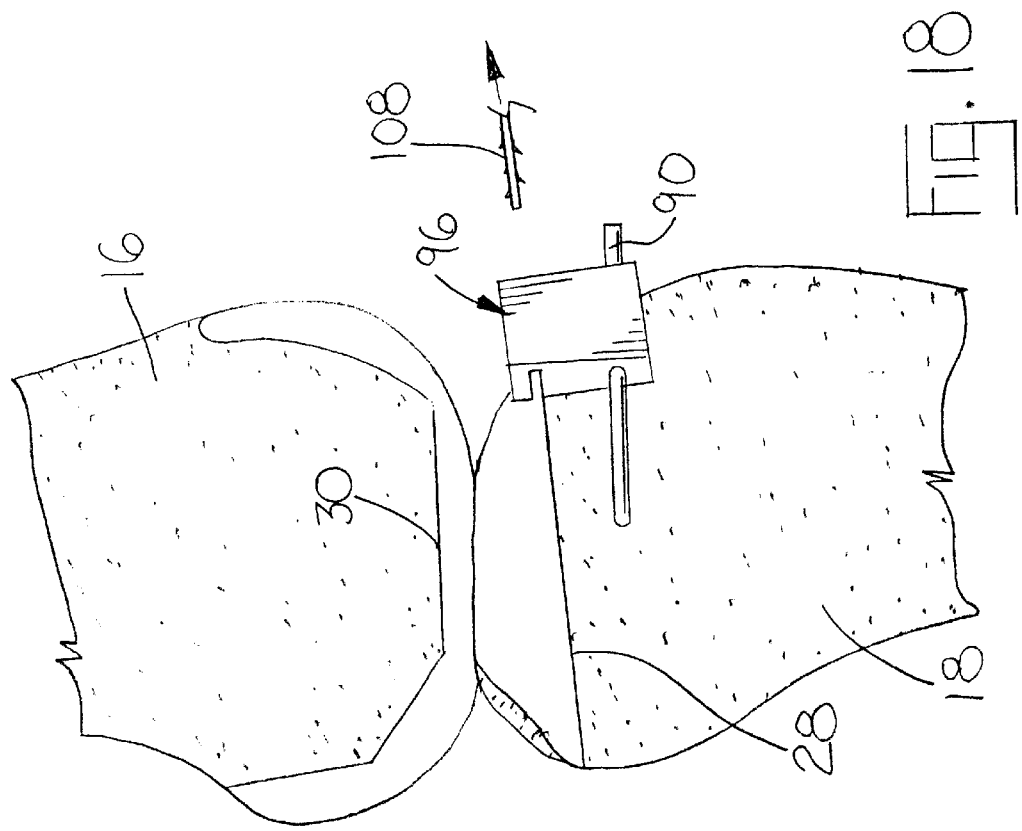

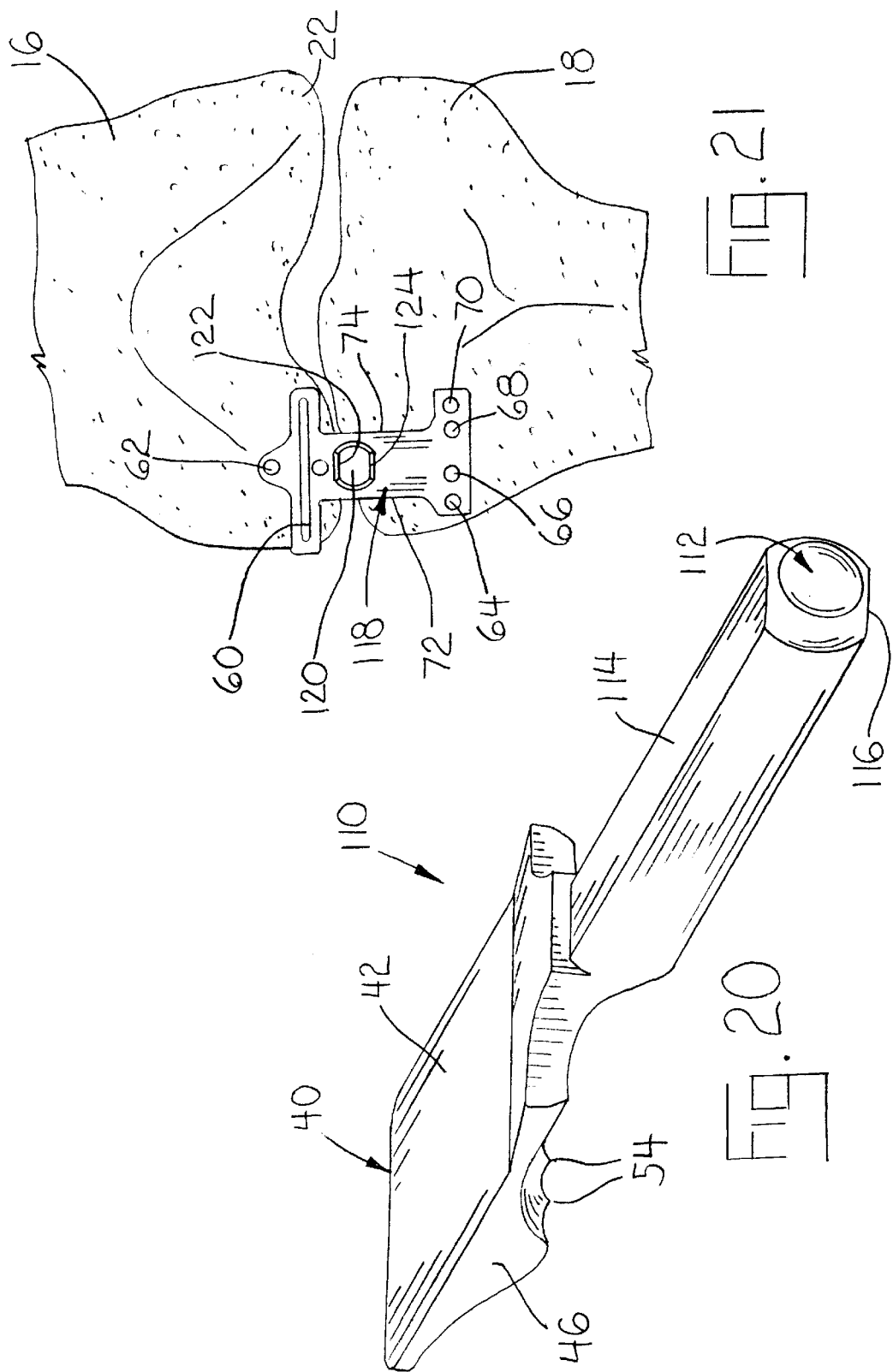

METHOD AND APPARATUS FOR RESECTING A DISTAL FEMUR AND A PROXIMAL TIBIA IN PREPARATION FOR IMPLANTING A PARTIAL KNEE PROSTHESIS

TECHNICAL FIELD

This invention relates to a method and apparatus for resecting a distal femur and a proximal tibia in preparation for implanting a partial knee prosthesis.

BACKGROUND OF THE INVENTION

Partial knee replacement surgery has become relatively common, and according to traditional practice, requires a relatively large incision in the patient in order to realign the patient's leg, remove any diseased bone and cartilage, and provide a proper surface for engagement with the tibial and femoral prostheses which must mate to form the partial knee replacement. Such large and complicated incisions increase surgical time and risk and also lengthen patient recovery. Accordingly, more recently minimally invasive techniques have become available, which greatly reduce the size of the required incision, thus providing more rapid healing and recovery for the patient. The instruments used in minimally invasive surgery clearly must be relatively small and are preferably uncomplicated, due to the space constraints within the knee. Further, these instruments must permit alignment of the knee and the proper preparation of the implant surfaces in order to receive and retain the prostheses.

When a patient's knee deteriorates, cartilage wears away, and the patient becomes bow-legged (or knock-kneed), depending upon which side of the knee is diseased. Accordingly, instruments must be used to reset the spacing between the distal femur and proximal tibia receiving the partial knee implant, to correct bow-leggedness and the patient's knock-knees. Overcorrection must be avoided, in order to avoid wear (and eventual deterioration) of the side of the knee not receiving the partial knee prosthesis.

SUMMARY OF THE INVENTION

The present invention provides a resecting kit which includes multiple spacers, each of which has a different spacing dimension. A surgeon selects the appropriate spacer with the amount of correction desired to align the patient's leg and installs the spacer with the spacing dimension between the distal femur and proximal tibia on the side of the knee which is to receive the partial knee prosthesis. The spacers have projecting stems, upon which a resector is installed in such a way that the resector may pivot around the stem. The resector is then aligned with the axis selected by the surgeon according to known methods, and is pinned to the femur and proximal tibia. A cut is then made in the femur after which the resector is removed while leaving the tibial pins in place, the pins being headless pins. A second resector is then installed on the pins to effect the required cut of the tibia. Other cuts are made in the femur according to known procedures, and the prostheses are then installed according to known procedures.

Accordingly, since they are relatively small, the spacers are relatively easy to install between the proximal tibia and distal femur. The spacers include a recess to clear the anterior tibial rise, such that the spacer is fully engaged both with the corresponding condyle and the tibial plateau where the prostheses are to be implanted. Since the spacers have no moving parts, minimal manipulation of the instruments within the saggital plane is required.

BRIEF DESCRIPTION OF THE DRAWINGS

FIG. 1 is a sagittal view of a partial knee prosthesis implanted on the distal femur and proximal tibia of a patient;

FIGS. 2–5 are side views of spacers used in the surgery resecting the proximal tibia and distal femur to accommodate implantation of the implant illustrated in FIG. 1;

FIGS. 10 and 11 are views similar to FIGS. 8 and 9 respectively but illustrating an alignment tower installed on the resector illustrated in FIGS. 8 and 9;

FIGS. 12 and 13 are views similar to FIGS. 10 and 11, but illustrating an alignment rod installed on the alignment tower;

FIGS. 16 and 17 are views similar to FIGS. 14 and 15, but illustrating another resector mounted on the spacer and further illustrating the manner in which the resection is performed;

FIGS. 18 and 19 are views similar to FIGS. 16 and 17 but illustrating the completed tibial cut and distal femoral cut;

FIG. 20 is a perspective view of a spacer according to another embodiment; and

FIG. 21 is an anterior view of the spacer of FIG. 20 installed between the distal femur and proximal tibia and having a resector installed on the spacer.

DESCRIPTION OF THE PREFERRED EMBODIMENT

As discussed above, the present invention relates to a method and apparatus for resecting a femur and tibia and for implanting a partial knee prosthesis, the resection being effected by using a resecting kit. The resecting kit includes a set of multiple spacers each having different spacing dimensions to permit the surgeon to adjust the spacing between the proximal tibia and distal femur at the side of the knee which the prosthesis is to be implanted, a pair of resectors for guiding resectioning of the tibia and femur, and other instruments for aligning the leg and preparing the knee for implantation of the partial knee prosthesis.

Figure 7:
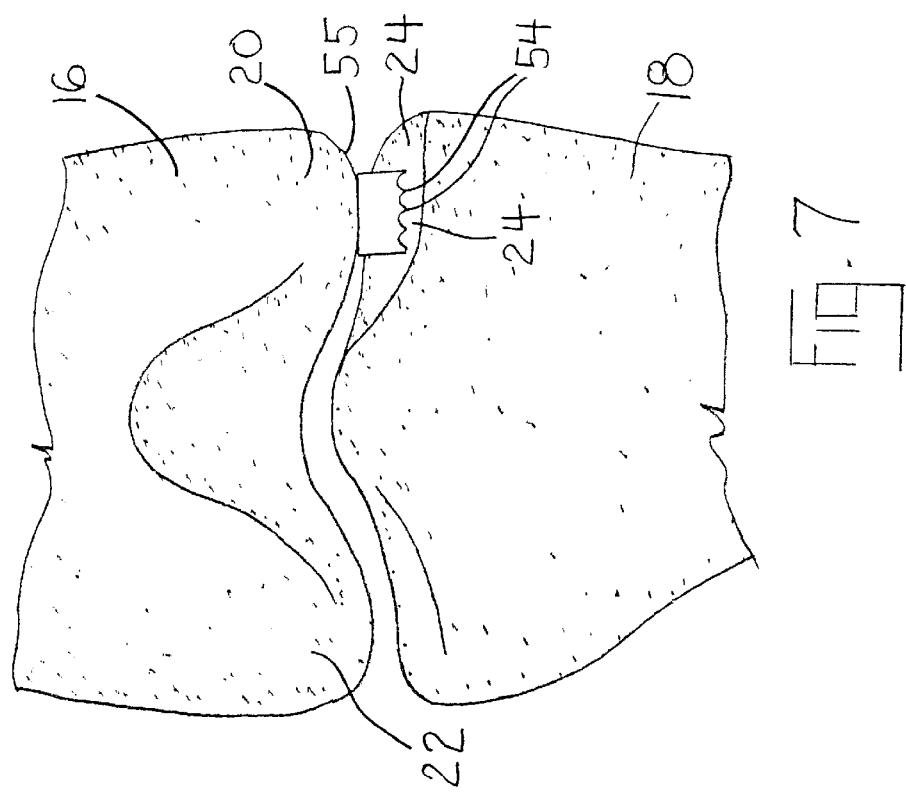
FIG. 7 is a posterior view taken along line 7—7 of FIG. 6.
Figure 6:
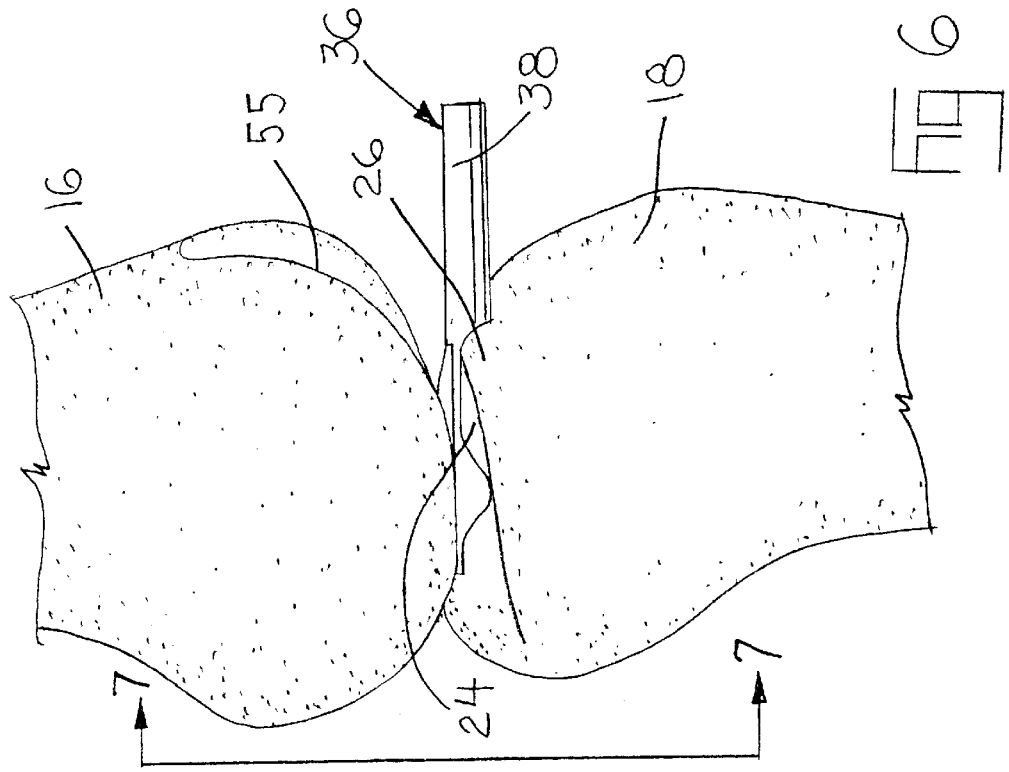
FIG. 6 is a sagittal view illustrating one of the spacers illustrated in FIGS. 2–5 installed between the distal femur and proximal tibia of a patient undergoing knee replacement surgery.

Referring now to the drawings, a partial knee prosthesis generally indicated by the numeral 10 includes a femoral prosthesis 12 and a tibial prosthesis 14. Femoral prosthesis 12 is implanted upon the distal femur 16, and the tibial prosthesis 14 implanted on the proximal tibial 18. As seen is FIGS. 7 and 9, the femur terminates in condyles 20 and 22. Since the prosthesis 10 may be used to replace either the lateral or medial condyle of the patient, femur 16 and proximal tibia 18 may represent either the right or left leg of the patient. The proximal tibia 18 terminates in a tibial plateau 24 bounded in part by the anterior tibial rise 26. In order to effect proper implantation of the prosthesis, a portion of the tibial plateau must be resected to provide a flat surface 28, which must be drilled in order to accommodate implantation of tibial prosthesis 14, which is then cemented into place. The distal femur must be resected to provide a distal femoral cut forming a surface 30, a posterior chamfer femoral cut forming a surface 32, and a posterior femoral cut forming a surface 34. Femoral prosthesis 12 includes anchors (not shown) which are received within holes drilled in one or more of the surfaces 30, 32 and 34 The present invention relates to a method and apparatus for effecting the resections forming the surfaces 28 and 30. Surfaces 32 and 34 are resected after the resections forming the surfaces 28 and 30 are effected. The cuts resulting in surfaces 32 and 34 are made in a conventional manner, such as by temporarily installing a drilling and cutting guide in the prior art on the surface 30 and then making the cuts necessary to form the surfaces 32 and 34.

To insure an acceptable result, it is desirable that the surfaces 28 and 30 held to as nearly parallel as possible in the lateral/medial plane, and that the surfaces 28, 30 diverge from each other about 6 degrees–8 degrees in the anterior to posterior plane. It is also necessary to align the patient's leg to correct bow-leggedness or the patient's knock-knees. If the diseased side of the joint is the medial side, the deterioration and the cartilage and any subsequent deterioration of the bone will cause the distance between the corresponding condyle and corresponding portion of the tibial plateau to narrow, resulting in the patient becoming bow-legged. On the other hand, if the diseased portion of the joint is on the lateral side, the patient becomes knock-kneed. In any case, it is necessary during surgery to effect implantation of the prosthesis 10 to realign the patient's leg and correct the bow-leggedness and/or knock-knees. The method and resection kit of the present invention permits the patient's leg to be straightened without over-correcting, since any over-correction will result in increased wear on the other side of the joint. Furthermore, the method and kit according to the present invention assures proper alignment of the surfaces 28 and 30.

After the joint has been opened by an incision of about two to three inches in length, the surgeon selects one of the spacers 36A–D illustrated in FIGS. 2–5 which the surgeon judges will provide the proper spacing between the distal femur 16 and proximal tibia 18 to correct the alignment of the patient's leg. In practice, many more spacers having different spacing dimensions will be provided; the spacers have been illustrated in FIGS. 2–5 for illustrative purposes only. Each of the spacers 36A–D include a stem 38 and an arm 40 extending from the stem. Small spacer 36A includes an arm 40 which includes a pair or opposed, substantially flat, parallel surfaces 42, 44. The spacing dimension of spacer 36A is the distance between the surfaces 42 and 44. Each of the remaining spacers 36B–D include an arm 40A–D having a substantial flat upper surface 42A with a bump 46 projecting from the surface 44. Each of the bumps 46 are defined by a curved surface 48 for a purpose described hereinafter. The spacing dimensions in each of the spacers 36B–D is the distance between the upper surface 42 and the maximum dimension of the bump 46. Curved surface 48 of the bump 46 cooperates with the surface 44 and transverse end surface 50 of the stem 38 to define a recess 52 therebetween. Transversely spaced, longitudinally extending keels 54 are provided on the bumps 46 (see FIG. 7).

After the patient's knee has been opened by the surgeon, the surgeon selects one of the spacers 36 which the surgeon judges will correct the patient's knock-knees or bow-leggedness and properly align the patient's leg. The surgeon manipulates the bump 46 (or the flat arm of spacer 36A) of the selected spacer over the anterior tibial rise 26 so that the anterior tibial rise 26 is received within the recess 52 of the spacer, the curved surface 48 engages the tibial plateau 24, and the upper flat surface 42 engages the contoured surface 55 of the condyle 20 at its closest approach to the tibial plateau 24. The keels 54 resist movement of the spacer 36 in the lateral-medial direction, but permit movement in the anterior-posterior direction to permit installation of the spacer such that the spacer separates the joint to correct the aforementioned alignment of the patient's leg. When the spacer is properly installed with the upper surface 42 engaging the contoured surface 55 at its, closest approach to the tibial plateau and with the curved surface 48 engaged with the tibial plateau, the surgeon then makes a judgment as to whether the patient's leg is properly aligned. If the surgeon decides that a different spacer is needed, the surgeon removes the first selected spacer and selects another spacer for installation between the distal femur 16 and proximal tibia 18. It will be noted that stem 38 of the selected spacer projects from the joint.

Figure 9:
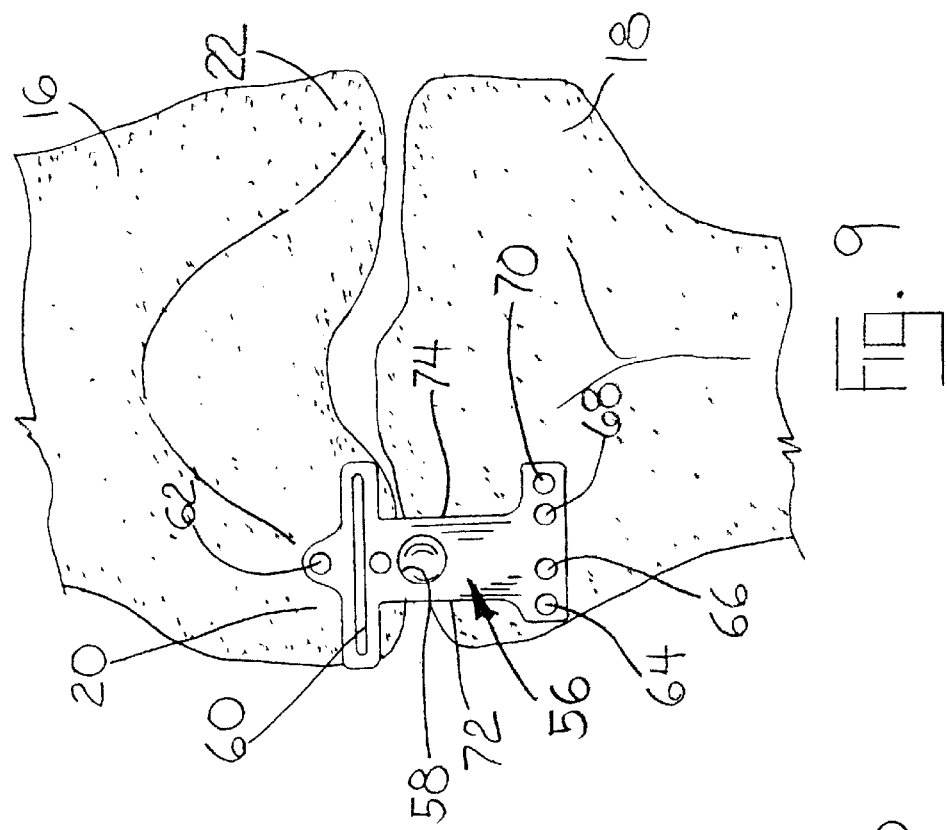
FIG. 9 is an anterior view taken substantially along lines 9—9 of FIG. 8.
Figure 8:
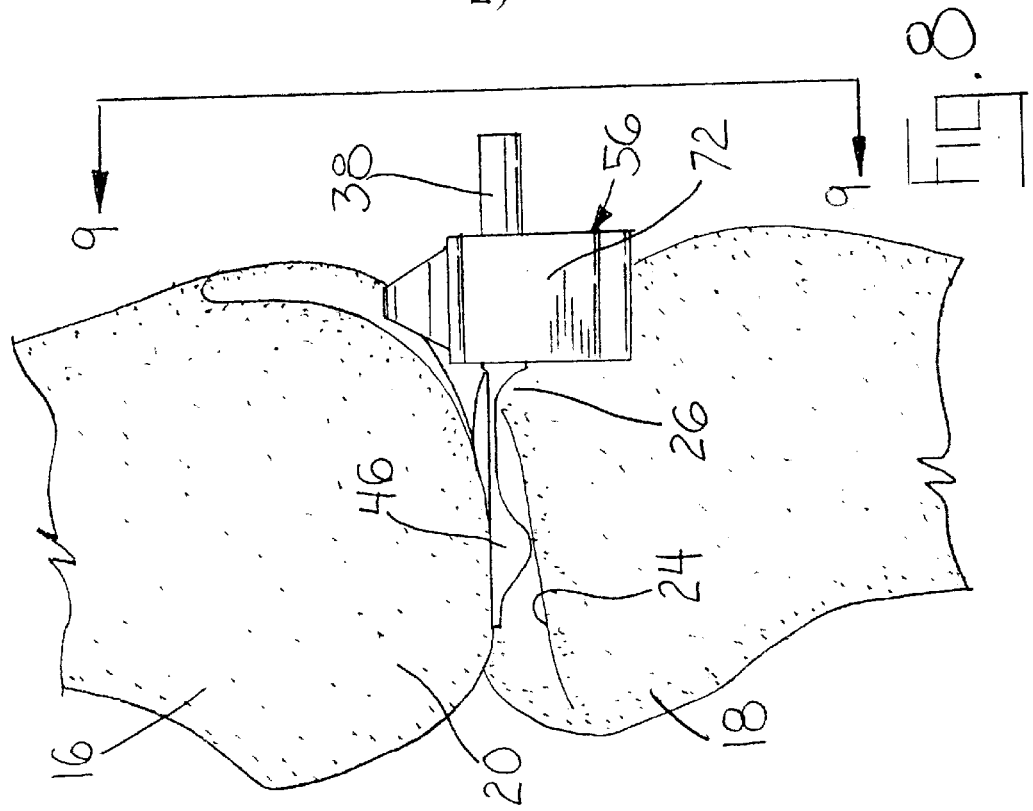
FIG. 8 is a sagittal view similar to FIG. 6 but illustrating a resector installed on the spacer illustrated in FIG. 6.

The surgeon then installs resector 56 on the stem 38 (FIGS. 8 and 9). The resector 56 includes a cylindrical aperture 58 slidably and rotatably engages the stem 38 to permit the resector 56 to pivot about the stem 38. The resector 56 further includes a slot 60 which is adapted to receive the blade of a saw that will effect cutting of the condyle 20. The resector 56 includes multiple apertures 62, 64, 66, 68, and 70, which are adapted to receive pins which will be hereinafter described. Furthermore, the resector 58 includes a pair of opposed, parallel side edges 72, 74.

After the resector is installed on the stem 38, an alignment tower generally indicated by the numeral 76 (FIGS. 10 and 11) is installed on the resector 56. The tower 76 includes a bifurcated end 78 including arms 80 that slidably engage the opposite side edges 72, 74 of the resector 56. The opposite end of the alignment tower 76 carries a cylinder 82, which projects transversely with respect to the alignment tower 76. A longitudinal opening 83 in alignment tower 76 receives the portion of stem 38 projecting from resector 56. Cylinder 82 defines an opening 84 extending transversely with respect to the alignment tower 76 which receives a longitudinally extending alignment rod 86. It is noted that, the side edges 72, 74 of resector 56 are perpendicular to the slot 60 in the resector 56, since the alignment tower 76 maintains the alignment rod 86 parallel to the side edges 72, 74, the axis of the alignment rod 86 will accordingly also be perpendicular to the slot 60. According to well-known techniques, the surgeon manipulates the alignment rod 86, which extends the entire length of the tibia, until the alignment rod 86 extends along an axis desired by the surgeon and which is chosen according to the surgeon's judgment and experience. In most cases, however, the selected axis will approximate the mechanical axis of the tibia. It will be noted that because of the curved surface 48 of the bump 46, the surgeon may rotate the spacer in the sagittal plane to permit the rod 86 to clear any obstacles, such as any projecting portions of the patient's leg or ankle.

Figure 15:
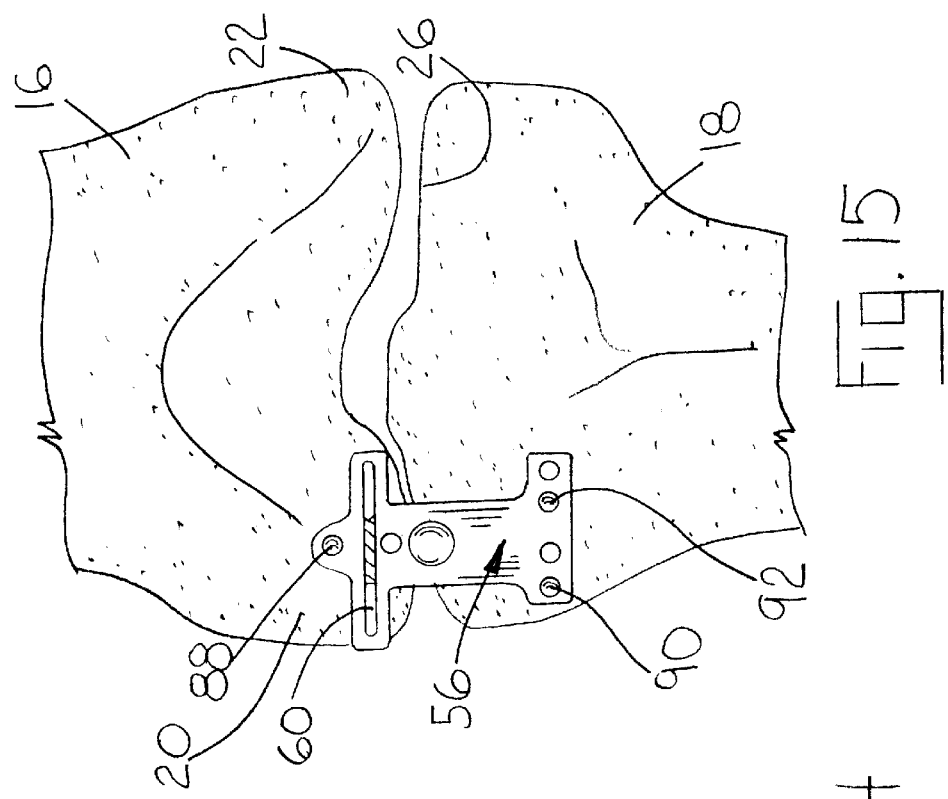
FIGS. 14 and 15 are views similar to FIGS. 8 and 9, but illustrating the manner in which the distal femur is resected using the resection kit in the present invention.
Figure 14:
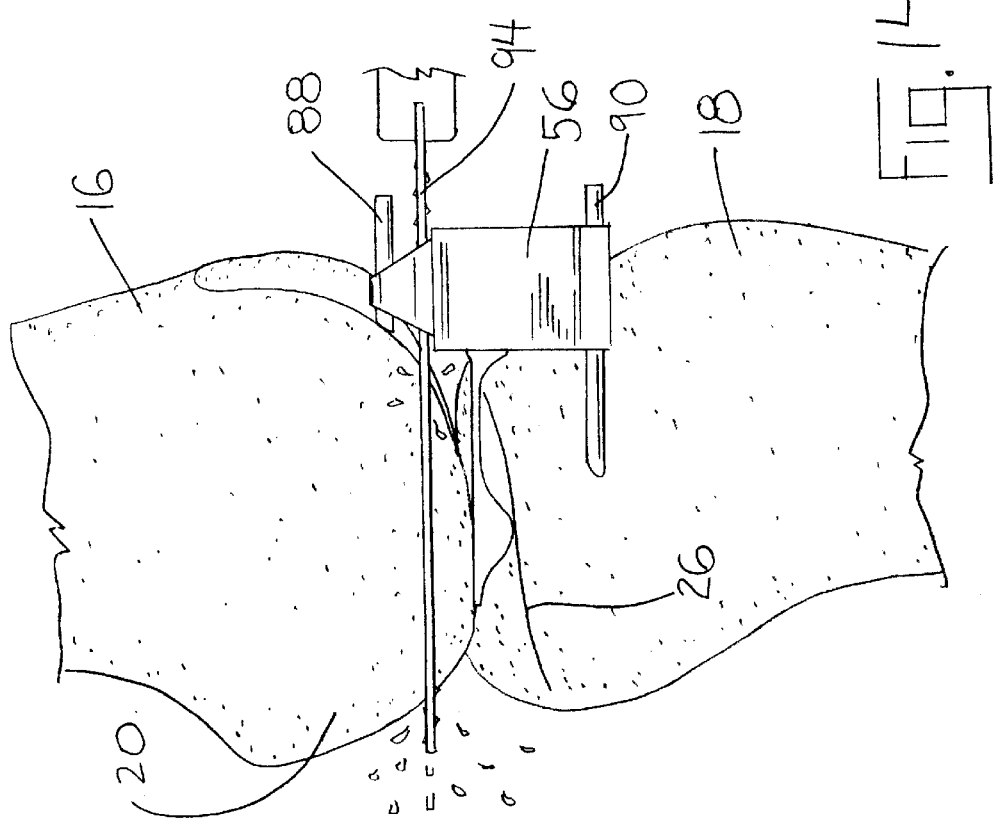

After the surgeon is satisfied with the alignment of the resector 56, headed or headless pins are installed in aperture 62 and headless pins are installed into a selected pair of apertures 64–70. As illustrated in FIGS. 14 and 15, pin 88 is installed in aperture 62 and pins 90 and 92 are installed in the apertures 64 and 68. The pins 88–92 are installed and secured in holes drilled in the distal femur and proximal tibia to thereby secure the resector 56 in place. As discussed above, the slot 60 of resector 56 will be perpendicular to the axis selected by the physician. After the resector 56 is pinned, the alignment rod 86 and alignment tower 76 are removed. A threaded opening 93 is provided which receives an appropriate threaded rod of a tool used to extract the alignment tower 76. A blade 94 of a conventional surgical saw is installed in the slot 60 and effects cutting of the condyle 20 to form the surface 30. Since the saw is guided by the slot 60, surface 30 will also be perpendicular to the axis selected by the physician.

After the surface 30 is cut, the pin 88 is removed, but the pins 90 and 92 are left in place. Since the pins 90, 92 are headless pins, the resector 56 may be pulled off of the pins by use of appropriate clamping tool (not shown) engaging the side edges 72, 74 so that the resector 56 may be pulled off of the pins 90, 92. After the surgeon has removed the resector 56, a second resector 96 is installed on the pins 90 and 92, care having been taken not to disturb the pins 90 and 92 in any way during the removal of the resector 56 and installation of the resector 96. The resector 96 is provided with a first set of apertures 98A, 98B, a second set of apertures 100A, 100B, a third set of apertures 102A, 102B, and a fourth set of apertures (through which the pins 90 and 92 extend as illustrated in FIGS. 16–17) 104A and 104B. Each of the aperture sets are spaced a distance to conform with the spacing between the pins 90 and 92, as established by use of the resector 56 as described above. The multiple sets of apertures are provided so that the surgeon may select the distance between the tibial cut and the distal femoral cut. The resector 96 is also provided with a slot 106. The resector is installed on the pins 90 and 92 and since the resector 96 has been designed with the slot 106 in a pre-established relationship with respect to the slot 60, the cut formed by the saw blade 108 through the slot 106 has the same relationship to the distal femoral cut 32. That is, the tibial cut formed by saw blade 108 in slot 106 in the resector 96 will be parallel to the horizontal femoral of surface 32 in the laterally-medial plane, and will have the proper diverging angle in the anterior posterior plane. After the tibial surface 28 is formed, the resector 96 is removed from the pins 90 and 92. The aforementioned fixture (not shown) is mounted on the surface 32 to guide resection of the surfaces 32, 34, and to drill the necessary apertures (not shown) to mount the femoral prosthesis 30. Similarly, a template (not shown) is used to drill the necessary mounting holes in the tibial surface 28. The prostheses 12 and 14 can then be installed according to known procedures.

Referring now to the embodiment of FIGS. 20 and 21, elements the same or substantially the same as those in the embodiment of FIGS. 1–19 retain the same reference numeral. A spacer generally indicated by the numeral 110 for setting the spacing between the distal femur and proximal tibia has been selected by the surgeon from a set of spacers similar to the set illustrated in FIGS. 2–5. However, the stem 38 of the spacers illustrated in FIGS. 2–5 has been replaced on the spacer 110 by a stem 112 having flats 114, 116 on opposite sides thereof. Similarly, the resector 56 of the embodiment of FIGS. 1–19 has been replaced with a resector 118 in the embodiment of FIGS. 20 and 21, which differs from the resector 56 only in that the aperture 58 of resector 56 has been replaced in resector 118 with an aperture 120 which is shaped complementary to the stem 112 (that is, with opposite flats 122, 124) so that the stem 112 is slidably received in the aperture 120 but is prevented from rotating relative thereto.

Accordingly, when the alignment tower 76 is installed on the resector 118 (in exactly the same manner as described above with respect to the resector 56), the resector 118 will not rotate relative to the stem during the alignment procedure but instead will pivot the spacer 110 relative the distal femur and proximal tibia. Since the resector 118 is not rotated relative to the spacer, the surgeon is assured that the cut made by use of the resector 118 is at a predetermined distance from the upper surface 42 of the spacer and is parallel thereto, although the spacing between the distal femur and proximal tibia will be slightly different from that initially established by installation of the spacer 110. Some surgeons prefer to assure that the size of the cut is confirmed by the resector, even if the spacing between the bones may be affected slightly; accordingly, these surgeons may prefer to use the spacer 110 and resector 118.

What is claimed is:

1. Spacer for use in orthopedic surgery for establishing a known spacing dimension between contiguous ends of skeletal members, comprising a stem projecting from between said skeletal members when the spacer is installed therebetween and an arm extending from said stem, said arm having a bump on one side thereof and an engagement surface on the other side thereof, said spacing dimension being the distance between the engagement surface and the region of said bump of maximum distance from said engagement surface.

2. Spacer for use in orthopedic surgery as claimed in claim 1, wherein said bump is defined by a curved outer edge to permit limited rotation of said spacer about said curved outer edge in response to movement of the stem.

3. Spacer for use in orthopedic surgery as claimed in claim 1, wherein said bump includes transversely spaced keels to resist transverse movement of the spacer when the latter is installed between skeletal members.

4. Spacer for use in orthopedic surgery as claimed in claim 1, wherein said arm defines a recess means between said stem and said bump for accommodating a tibial rise.

5. Spacer for use in orthopedic surgery as claimed in claim 4, wherein said stem terminates in a transverse surface defining one edge of said recess.

6. Spacer for use in orthopedic surgery as claimed in claim 5, wherein said engagement surface opposite said bump is a substantially flat surface.

7. Spacer for use in orthopedic surgery as claimed in claim 3, wherein said stem is substantially cylindrical.

8. Spacer for use in orthopedic surgery as claimed in claim 3, wherein said stem includes flats on opposite sides of the stem.

9. The spacer of claim 1 wherein said engagement surface is opposite said bump.

10. Spacer kit for use in orthopedic surgery for establishing a known spacing dimension between contiguous ends of skeletal members, comprising multiple spacers each having a known spacing dimension, said spacers each having an arm for installation between said skeletal members and a stem extending from said arm, at least some of said spacers having a stem and an arm extending from said stem, said arm having a bump on one side thereof and an engagement surface on the other side thereof, said spacing dimension being the distance between the engagement surface and the region of said bump of maximum distance from said engagement surface, said bump having a height different for each of said spacers whereby a selected spacer may be used to establish a corresponding spacing dimension.

11. Spacing kit as claimed in claim 10, wherein the arm of at least one of said spacers is a substantially flat blade having opposite substantially flat surfaces, said spacing dimension being the thickness of said blade between said substantially flat surfaces.

12. Spacing kit as claimed in claim 11, wherein each bump is defined by a curved outer edge to permit limited rotation of said spacer about said curved outer edge in response to movement of the stem.

13. Spacing kit as claimed in claim 11, wherein each bump includes transversely spaced keels to resist transverse movement of the spacer when the latter is installed between skeletal members.

14. Spacing kit as claimed in claim 11, wherein each bump cooperates with its arm and stem to define a recess means therebetween for accommodating a tibial rise.

15. Spacing kit as claimed in claim 10, wherein each bump is defined by a curved outer edge to permit limited rotation of said spacer about said curved outer edge in response to movement of the stem.

* * * * *